United States Patent
Mandal

(10) Patent No.: US 6,957,700 B2
(45) Date of Patent: Oct. 25, 2005

(54) SELF-CALIBRATED ULTRASONIC METHOD OF IN-SITU MEASUREMENT OF BOREHOLE FLUID ACOUSTIC PROPERTIES

(75) Inventor: Batakrishna Mandal, Missouri City, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 5 days.

(21) Appl. No.: 10/705,184

(22) Filed: Nov. 11, 2003

(65) Prior Publication Data

US 2004/0128072 A1 Jul. 1, 2004

Related U.S. Application Data

(62) Division of application No. 09/927,067, filed on Aug. 9, 2001, now Pat. No. 6,712,138.

(51) Int. Cl.[7] .............................................. E21B 47/06
(52) U.S. Cl. ....................... 166/250.01; 175/48; 367/25; 367/32
(58) Field of Search ......................... 166/250.01, 254.2; 175/48, 50; 367/25, 32; 73/64.53, 152.16, 152.32, 152.47, 152.58; 181/102–106, 122

(56) References Cited

U.S. PATENT DOCUMENTS

| | | | | |
|---|---|---|---|---|
| 4,052,887 A | * | 10/1977 | Sheridan et al. | 73/592 |
| 4,571,693 A | * | 2/1986 | Birchak et al. | 702/54 |
| 4,709,357 A | * | 11/1987 | Maki, Jr. | 367/35 |
| 4,928,269 A | * | 5/1990 | Kimball et al. | 367/35 |
| 5,031,467 A | | 7/1991 | Rambow | |
| 5,216,638 A | * | 6/1993 | Wright | 367/35 |
| 6,041,861 A | | 3/2000 | Mandal et al. | |
| 6,189,383 B1 | | 2/2001 | Tello et al. | |

FOREIGN PATENT DOCUMENTS

| | | |
|---|---|---|
| EP | 0 483 491 A1 | 5/1992 |
| JP | 61-38559 | 2/1986 |
| WO | WO 99/31354 | 6/1999 |

OTHER PUBLICATIONS

Search Report—02 10 116 French Patent Application Search Report Dated Mar. 23, 2004 (2 p.).

* cited by examiner

*Primary Examiner*—Zakiya Walker
(74) *Attorney, Agent, or Firm*—Conley Rose, P.C.

(57) ABSTRACT

Tools and methods are provided that determine the acoustic impedance of drilling fluid using reflections from a precise metal disk. Because the reverberation characteristics of an acoustic wave depend in part on the acoustic wave shape, the first reflection from the metal disk may be used to calibrate the measurement. A method for determining a borehole fluid property includes (i) generating an acoustic signal within a borehole fluid, (ii) receiving reflections of the acoustic signal from the fluid, and (iii) analyzing a reverberation portion of the acoustic signal to determine the property. The analyzing of the reverberation portion may include obtaining a theoretical reverberation signal and relating the measured reverberation signal with the theoretical reverberation signal to determine the borehole fluid property.

20 Claims, 6 Drawing Sheets

SELF-CALIBRATED ULTRASONIC METHOD OF IN-SITU MEASUREMENT OF BOREHOLE FLUID ACOUSTIC PROPERTIES

CROSS-REFERENCE TO RELATED APPLICATIONS

This application is a divisional of U.S. patent application Ser. No. 09/927,067 which was filed Aug. 9, 2001 now U.S. Pat. No. 6,712,138.

STATEMENT REGARDING FEDERALLY SPONSORED RESEARCH OR DEVELOPMENT

Not Applicable.

BACKGROUND OF THE INVENTION

1. Field of the Invention

The present invention relates generally to oil well logging and monitoring. More particularly, the present invention relates to determining the acoustic properties of a borehole fluid.

2. Description of the Related Art

To recover oil and gas from subsurface formations, wellbores or boreholes are drilled by rotating a drill bit attached at an end of a drill string. The drill string includes a drill pipe or a coiled tubing that has a drill bit at its downhole end and a bottom hole assembly (BHA) above the drill bit. The wellbore is drilled by rotating the drill bit by rotating the tubing and/or by a mud motor disposed in the BHA. A drilling or wellbore fluid commonly referred to as the "mud" is supplied under pressure from a surface source into the tubing during drilling of the to wellbore. The drilling fluid operates the mud motor (when used) and discharges at the drill bit bottom. The drilling fluid then returns to the surface via the annular space (annulus) between the drill string and the wellbore wall or inside. Fluid returning to the surface carries the rock bits (cuttings) produced by the drill bit as it disintegrates the rock to drill the wellbore.

A wellbore is overburdened when the drilling fluid column pressure is greater than the formation pressure. In overburdened wellbores, some of the drilling fluid penetrates into the formation, thereby causing a loss in the drilling fluid and forming an invaded zone around the wellbore. It is desirable to reduce the fluid loss into the formation because it makes it more difficult to measure the properties of the virgin formation, which are required to determine the presence and retrievability of the trapped hydrocarbons. In underbalanced drilling, the fluid column pressure is less than the formation pressure, which causes the formation fluid to enter into the wellbore. This invasion may reduce the effectiveness of the drilling fluid.

A substantial proportion of the current drilling activity involves directional boreholes (deviated and horizontal boreholes) and/or deeper boreholes to recover greater amounts of hydrocarbons from the subsurface formations and also to recover previously unrecoverable hydrocarbons. Drilling of such boreholes require the drilling fluid to have complex physical and chemical characteristics. The drilling fluid is made up of a base such as water or synthetic material and may contain a number of additives depending upon the specific application. A major component in the success the drilling operation is the performance of the drilling fluid, especially for drilling deeper wellbores, horizontal wellbores and wellbores in hostile environments (high temperature and pressure). These environments require the drilling fluid to excel in many performance categories. The drilling operator and the mud engineer determine the type of the drilling fluid most suitable for the particular drilling operations and then utilize various additives to obtain the desired performance characteristics such as viscosity, density, gelation or thixotropic properties, mechanical stability, chemical stability, lubricating characteristics, ability to carry cuttings to the surface during drilling, ability to hold in suspension such cuttings when fluid circulation is stopped, environmental harmony, non-corrosive effect on the drilling components, provision of adequate hydrostatic pressure and cooling and lubricating impact on the drill bit and BHA components.

A stable borehole is generally a result of a chemical and/or mechanical balance of the drilling fluid. With respect to the mechanical stability, the hydrostatic pressure exerted by the drilling fluid in overburdened wells is normally designed to exceed the formation pressures. This is generally controlled by controlling the fluid density at the surface. To determine the fluid density during drilling, the operators take into account prior knowledge, the behavior of rock under stress, and their related deformation characteristics, formation dip, fluid velocity, type of the formation being drilled, etc. However, the actual density of the fluid is not continuously measured downhole, which may be different from the density assumed by the operator. Further, the fluid density downhole is dynamic, i.e., it continuously changes depending upon the actual drilling and borehole conditions, including the downhole temperature and pressure. Thus, it is desirable to determine density of the wellbore fluid downhole during the drilling operations and then to alter the drilling fluid composition at the surface to obtain the desired density and/or to take other corrective actions based on such measurements.

As noted above, an important function of the drilling fluid is to transport cuttings from the wellbore as the drilling progresses. Once the drill bit has created a drill cutting, it should be removed from under the bit. If the cutting remains under the bit it is redrilled into smaller pieces, adversely affecting the rate of penetration, bit life and mud properties. The annular velocity needs to be greater than the slip velocity for cuttings to move uphole. The size, shape and weight of the cuttings determine the viscosity necessary to control the rate of settling through the drilling fluid. Low shear rate viscosity controls the carrying capacity of the drilling fluid. The density of the suspending fluid has an associated buoyancy effect on cuttings. An increase in density usually has an associated favorable affect on the carrying capacity of the drilling fluid. In horizontal wellbores, heavier cuttings can settle on the bottom side of the wellbore if the fluid properties and fluid speed are not adequate. Cuttings can also accumulate in washed-out zones. Determining the density of the fluid downhole provides an indication of whether cuttings are settling or accumulating at any place in the wellbore.

In the oil and gas industry, various devices and sensors have been used to determine a variety of downhole parameters during drilling of wellbores. Such tools are generally referred to as the measurement-while-drilling (MWD) tools. The general emphasis of the industry has been to use MWD tools to determine parameters relating to the formations, physical condition of the tool and the borehole. Very few measurements are made relating to the drilling fluid. The majority of the measurements relating to the drilling fluid are made at the surface by analyzing samples collected from the fluid returning to the surface. Corrective actions are taken based on such measurements, which in many cases take a long time and do not represent the actual fluid properties downhole.

SUMMARY OF THE INVENTION

The problems outlined above are in large part addressed by a self-calibrated ultrasonic method of in-situ measurement of borehole fluid acoustic properties. In a preferred embodiment of the present invention, a method for determining a borehole fluid property includes (i) generating an acoustic signal within a borehole fluid, (ii) receiving reflections of the acoustic signal from the fluid, and (iii) analyzing a reverberation portion of the acoustic signal to determine the property. The analyzing of the reverberation portion may include obtaining a theoretical reverberation signal and relating the measured reverberation signal with the theoretical reverberation signal to determine the borehole fluid property.

In another preferred embodiment of the present invention, a processor adapted to provide real-time estimates of a borehole fluid property includes an input terminal and a processing portion. The input terminal receives a data signal corresponding to a reflected acoustic wave. The processing portion separates the data signal into a first reflection portion and a resonance portion and convolves the first reflection portion response to yield a theoretical reverberation response.

In yet another preferred embodiment of the present invention, a tool for measuring borehole fluid properties includes a body, an acoustic transducer, and a metal disk. The body houses the transducer and metal disk. A borehole fluid enters the tool through an opening in the body, flows in between the transducer and metal disk where it is measured, and exits the tool.

Thus, the present invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figure 1A:
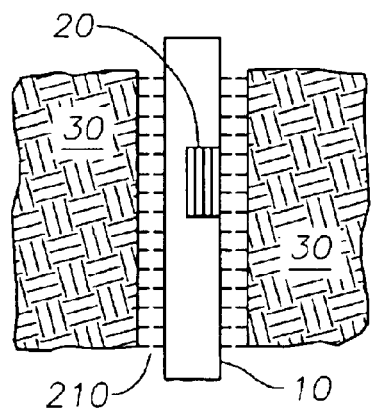
FIG. 1A is a general schematic showing a tool in a preferred embodiment.

FIG. 1A illustrates a general overview of a tool submerged downhole. Shown are tool 10, fluid vent 20, formation 30, and well fluid 210. Fluid vent 20 provides a means for well fluid 210 to enter and exit tool 10. While in tool 10, well fluid 210 is measured for its acoustic properties.

Figure 1B:
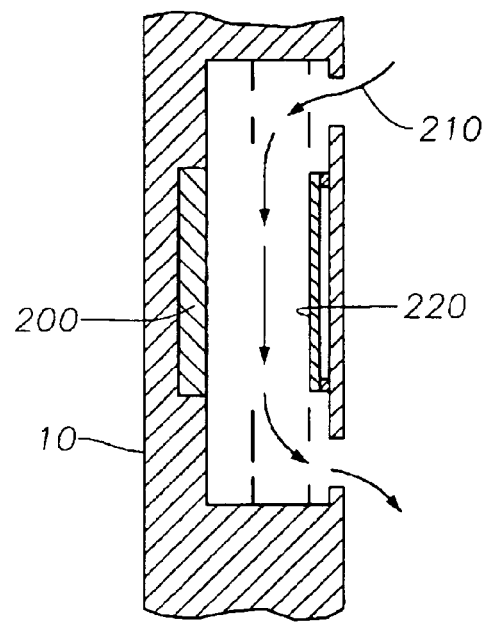
FIG. 1B is a cut-away view illustrating component parts of FIG. 1A.

FIG. 1B is a cross-sectional view of the tool showing acoustic measurement components. Inside tool 10, where fluid vent 20 is located, are acoustic transducer 200 and metal disk 220. As can be seen, well fluid 210 enters tool 10, flows between acoustic transducer 200 and metal disk 220, and exits tool 10.

Figure 2:
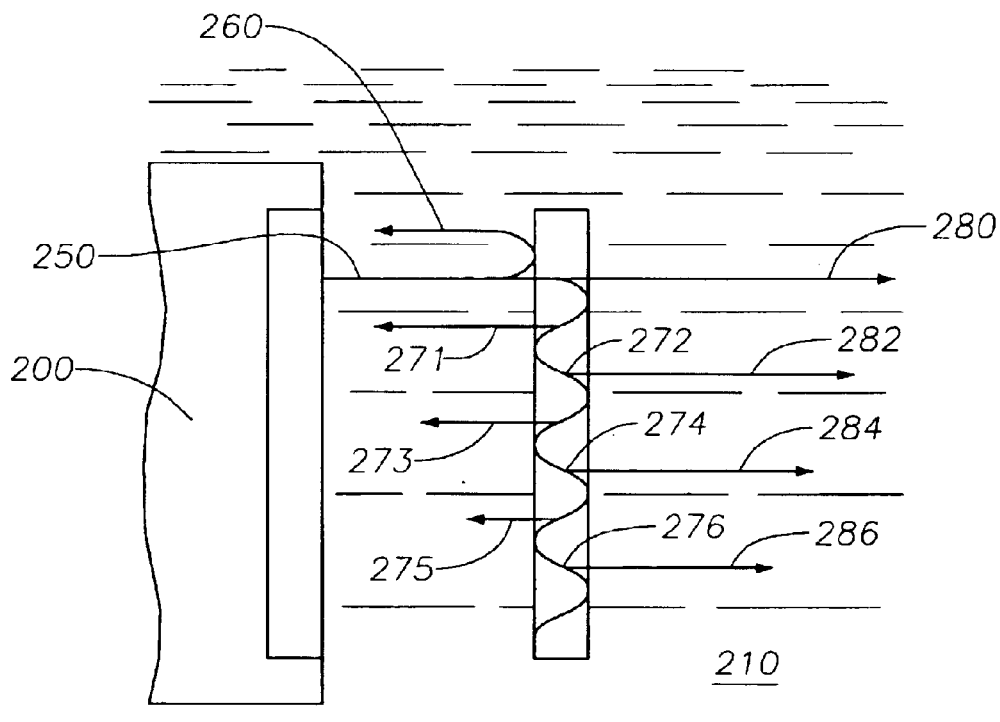
FIG. 2 illustrates waveform reflection and reverberation.

FIG. 2 illustrates the acoustic wave path and metal disk reverberations for a downhole acoustic wave. Shown are acoustic transducer 200, well fluid 210 and metal disk 220. Well fluid 210 and disk 220 each has its own impedance, labeled $Z_m$ and $Z_s$, respectively. Also shown is acoustic signal 250, including first reflected portion 260, disk reverberation portions 271–276 and transmitted wave portions 280, 282, 284 and 286 through the disk in the same well fluid.

To measure the reflection coefficient of the well fluid, the acoustic transducer 200 sends out acoustic signal 250, which is preferably an ultrasonic impulse with a characteristic frequency of about 500 kHz, then switches to the receive mode. The impulse frequency is preferably set at the expected resonance frequency of the disk. The acoustic signal 250 travels through the well fluid 210 and strikes the disk 220. The largest portion of the energy of the impulse is reflected back to the transducer as reflected portion 260 while a small amount of signal enters the disk as wave 280. When the well fluid 210 is water, the reflected wave form has an amplitude of about 93% of the initial impulse. The portion of the signal that entered the disk is reflected back and forth between the disk/fluid interface and the disk/tool interface, as illustrated by wave reverberations 271–276. At each reflection some energy is transmitted through the interface, dependent on the acoustic impedance contrast, and is either directed back toward the transducer or out into the tool. The signal inside the disk is quickly dissipated in this manner at a rate directly dependent on the acoustic impedance of the material outside the disk according to the equation:

$$R_1 = (Z_1 - Z_2)/(Z_1 + Z_2) \quad (1)$$

where $R_1$ is the reflection coefficient, and $Z_1$ and $Z_2$ are the impedances of the materials at the interface in question. In a preferred embodiment, the thickness of the metal disk is set to one half of the resonant wavelength of the transducer signal.

Figure 3:
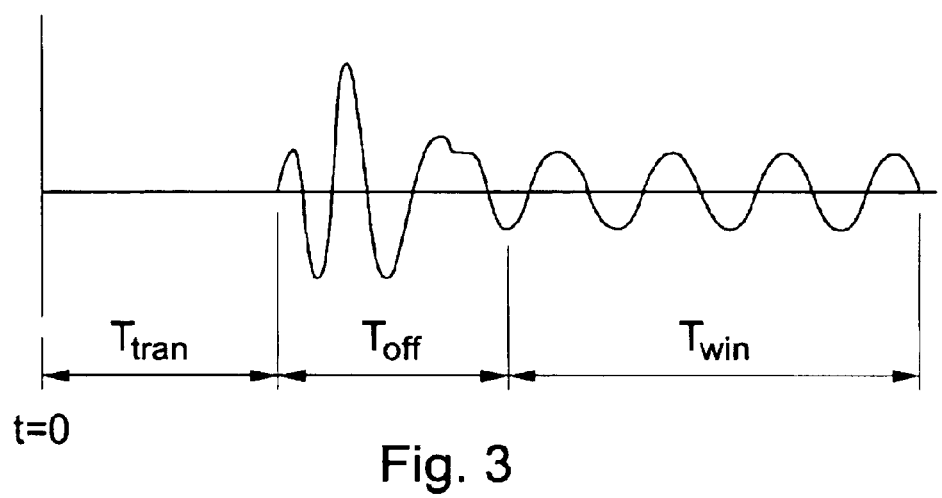
FIG. 3 is a graph showing a received acoustic waveform.

The acoustic transducer 200, now acting as a receiver or transducer, sees a waveform consisting of a loud initial reflection followed by an exponentially decaying reverberation signal. FIG. 3 illustrates the measured acoustic waveform received at the transducer 200. If time t=0 is the time of generation of the acoustic wave at the acoustic transmitter, then the time $T_{tran}$ represents the transit time (the time for the travel of this acoustic wave to the disk and back to the transceiver). Since the distance is fixed, the transit time $T_{tran}$ provides an indication of the acoustic velocity of the fluid. Also shown in FIG. 3 are the Time Offset, $T_{off}$, and the Resonance Window, $T_{win}$, both of whose significance is explained below.

Figure 4:
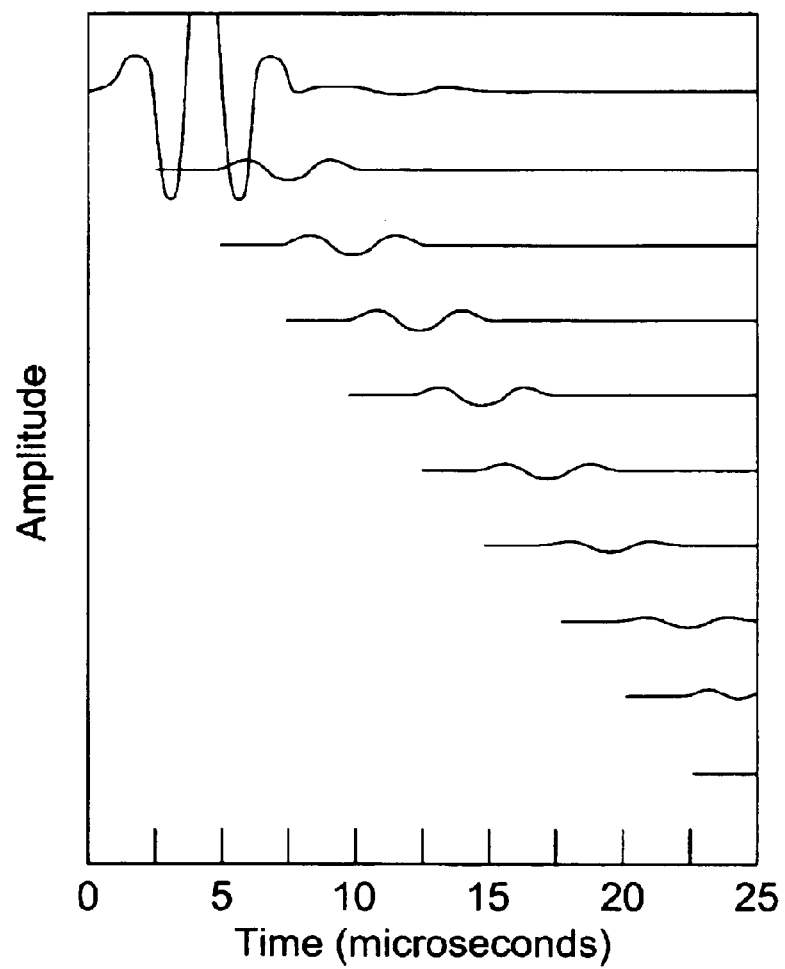
FIG. 4 is a diagram illustrating the component parts of FIG. 3.

FIG. 4 illustrates the individual waveforms, both first reflection and reverberations, that sum to provide the waveform of FIG. 3. The waveform received by the transducer is the sum of the initial reflection waveform with each reverberation waveform, where each reverberation is delayed an amount proportional to the width of the disk. Further, because the acoustic transducer is not a perfect transmitter, it "rings" somewhat upon the transmission of an acoustic wave. This transducer "ringing" also is included in the detected waveform, and may be accounted for by the present invention.

Figure 5B:
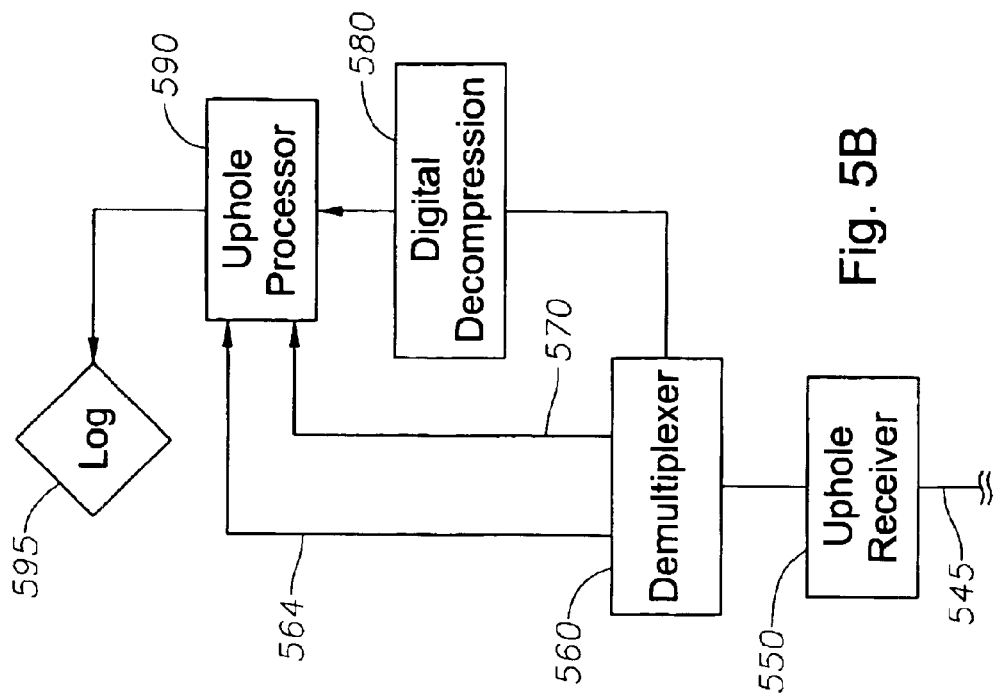
FIG. 5B is a diagram of the above ground system built in accord with a preferred embodiment.
Figure 5A:
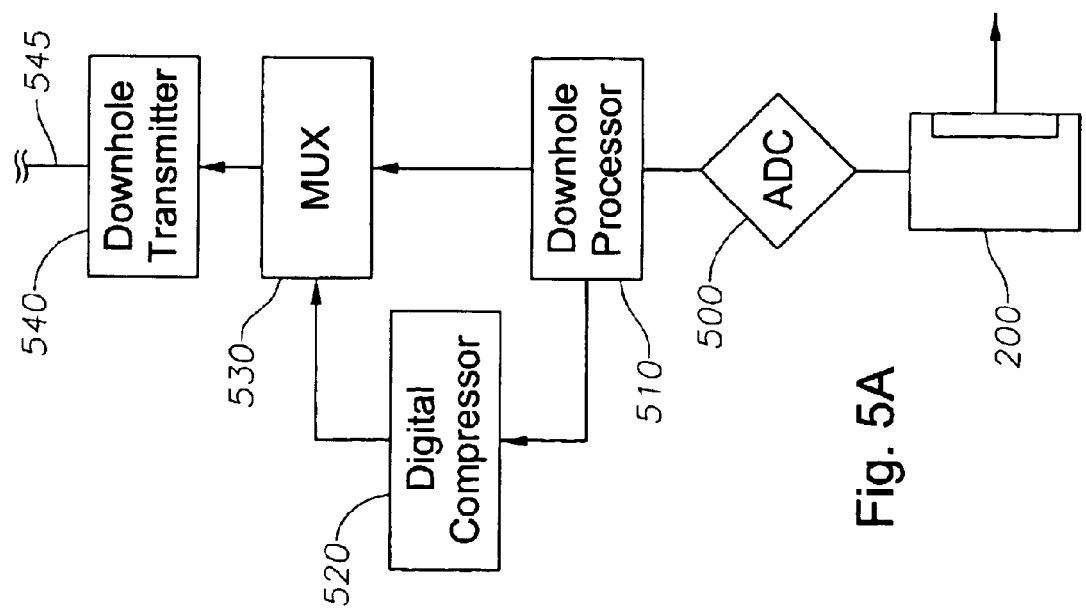
FIG. 5A is a diagram of a subterranean system built in accord with a preferred embodiment.

FIG. 5 illustrates a device built in accord with a preferred embodiment. Shown in FIG. 5A is acoustic transducer 200, analog-to-digital converter 500, a processor 510 for recording start time and gain, waveform compression chip 520, and multiplexer 530. Waveform compression chip 520 could alternately be part of a processor. Also shown are downhole transmitter 540 connected to multiplexer 530 and telemetry cable 545. Referring now to FIG. 5B, at the surface are located uphole receiver 550, demultiplexer 560, transmission line 564 carrying tool information to processor 590 for a data log 595, transmission line 570 carrying gain and start time information to uphole processor 590, and waveform decompression chip 580. Attached to decompression chip 580 is processor 590. Processor 590 generates data suitable for a log 595.

Referring now to both FIGS. 5A and 5B, acoustic transducer 200 collects data of metal disk reflection and reverberation. This acoustic waveform is digitized by analog-to-digital converter 500 and sent to processor 510, which detects the first reflection from the digitized signal. Processor 510 then computes the relevant start time and transit time. Because the total waveform data may be greater than the bandwidth capacity of transmission line 545, digital compression 520 is preferably performed. Suitable compressions include wavelet and ADPCM (Adaptive Differential Pulse Code Modulation) techniques, which work well for smoothly varying data. The compressed waveform from digital compression chip 520 is then multiplexed 530 with the other tool information. Downhole transmitter 540 sends this multiplexed data to the surface. Sending the data to the surface allows processing by faster, more sophisticated machinery.

Referring now to both FIGS. 5A and 5B, acoustic transceiver 200 collects data of metal disk reflection and reverberation. This acoustic waveform is digitized by analog-to-digital converter 500 and sent to processor 510, which detects the first reflection from the digitized signal. Processor 510 then computes the relevant start time and transit time. Because the total waveform data may be greater than the bandwidth capacity of transmission line 545, digital compression 520 is preferably performed. Suitable compressions include wavelet and ADPCM (Adaptive Differential Pulse Code Modulation) techniques, which work well for smoothly varying data. The compressed waveform from digital compression chip 520 is then multiplexed 530 with the other tool information. Downhole transmitter 540 sends this multiplexed data to the surface. Sending the data to the surface allows processing by faster, more sophisticated machinery.

This multiplexed data is received by uphole receiver 550 and is separated into component parts by demultiplexer 560. Waveform decompression chip 580 provides the reconstructed waveform to processor 590, which also receives start time information. Upon the determination of the reflection coefficient of the well fluid, processor 590 combines with position information and creates a log 595.

Figure 6:
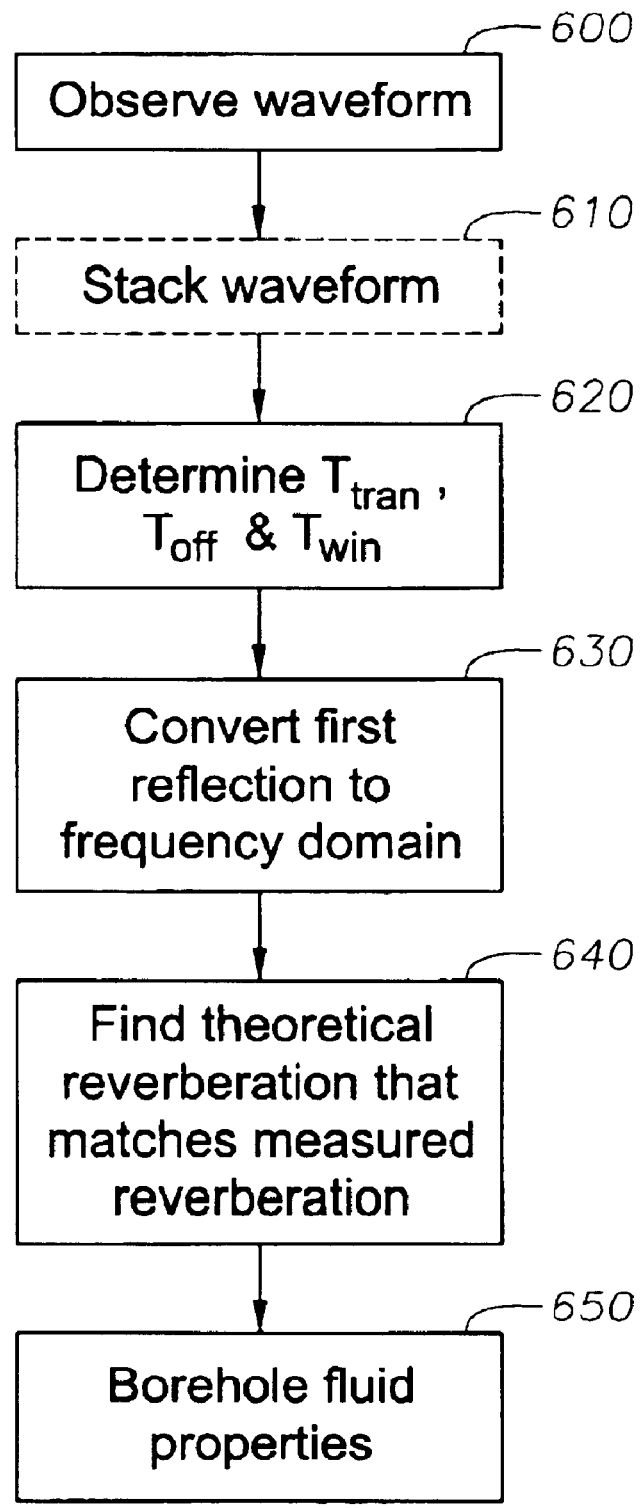
FIG. 6 is a general flow diagram of a preferred embodiment.

FIG. 6 illustrates a general method for the present invention. In block 600, an observed waveform is provided uphole for processing. In some embodiments, it may be desirable to stack waveforms (block 610). The waveform's transit time ($T_{tran}$) is obtained in block 620, as well as the time windows $T_{off}$ and $T_{win}$. The definition of transit time was explained above with reference to FIG. 3 and may be easily measured by a first reflection detector portion of processor 510. $T_{off}$ and $T_{win}$ are then selected to obtain a time window $T_{win}$ that contains reliable reverberation information. $T_{off}$, measured from the time of receipt for the initial reflection, is a time window that encompasses the initial reflection. As such, its duration is dependent upon the duration of the acoustic impulse transmitted by acoustic transducer 200 and the nature of the drilling fluid. $T_{off}$ also preferably accounts for error introduced because of the real-world shortcomings of the acoustic transducer (transducer "ringing"), and thus $T_{off}$ may be slightly longer than if chosen theoretically. Nonetheless, $T_{off}$ is about 15 microseconds. $T_{win}$ is juxtaposed with $T_{off}$ and is a time window of interest because $T_{win}$ contains reverberation information uncontaminated by the first reflection. The duration of $T_{win}$ should be brief enough so that noise and reverberations occurring in the tool 10 do not make unreliable the received disk reverberation waveforms. Nonetheless, so that a reliable wave train containing sufficient data is obtained, $T_{win}$ preferably includes at least four reverberations. Thus, $T_{win}$ is about 12.8 microseconds.

The tool calibration may be obtained as follows. First, the reflection waveform defined by $T_{off}$ is transformed to the frequency domain by use of DFT (Discrete Fourier Transform). Referring back to FIG. 6, proper modeling applied to the first reflection portion 260, as defined by $T_{off}$, gives a theoretical prediction of what the reverberation waveform contained in $T_{win}$ should look like. To accomplish this, in block 630 the first reflection signal is transformed by Fast Fourier Transform (FFT) into its frequency domain equivalent. This yields S(ω). Because the modeling is done in the frequency domain, amplitude and phase errors are eliminated. This error elimination simplifies mathematical processing (and hence faster processing is obtained).

Alternately, instead of transforming each first reflection individually, to enhance accuracy, the first reflections from multiple firings may first be averaged and the result transformed in block 630 by FFT processing into the frequency domain to yield S(ω). A most reliable first reflection average may be obtained by discarding first reflections that have amplitudes above or below a preset deviation from a moving average of preceding first reflections.

In block 640, a theoretical prediction of the reverberation waves is obtained by multiplying (convolution in time domain) the frequency-domain first reflection signal S(ω) with a frequency-domain theoretical response equation R(ω) to obtain a frequency domain version X(ω) of the reverberation signal x(t). Assuming a flat metal disk, the theoretical frequency domain response may be modeled by the following:

$$R(\omega) = \frac{Z_m - Z_s}{Z_m + Z_s} + \frac{\frac{4Z_m Z_s (Z_s - Z_m)}{(Z_m + Z_s)^3} e^{-i2\omega \frac{C_T}{V_s}}}{1 - \left(\frac{Z_s - Z_m}{Z_m + Z_s}\right)^2 e^{-i2\omega \frac{C_T}{V_s}}} \quad (2)$$

Where
R(ω)=the reflection coefficient for angular frequency ω
$Z_m$, $Z_s$, =impedances for mud and metal disk, respectively
$V_s$=the speed of sound in the metal disk, and
$C_T$=the thickness of the metal disk.

The above equation assumes that the transducer generates waves having normal (i.e., perpendicular) incidence on the disk. $V_s$, $Z_s$, and $C_T$ can be measured very precisely as basic physical properties of the metal disk.

In block 640 the frequency domain signal X(ω) is transformed back into the time domain by use of an Inverse Fast Fourier Transform (IFFT). As such, block 640 provides the theoretical reverberation response x(t) for the observed initial reflection waveform(s) in the time domain. This theoretical reverberation response is also a function of the borehole fluid impedance $Z_m$. Once the results are converted to the time domain, a relationship is established between the theoretical response and the received response. Next, a method is used to determine the borehole fluid properties in block 650.

Two embodiments for relating theoretical and measured responses in block 640 include 1) a curve fitting method and 2) a non-linear waveform inversion method. Both methods calculate theoretical waveform response based on Equation 2. However, the curve fitting method uses fewer theoretical modeling steps than the inversion method.

Figure 7A:
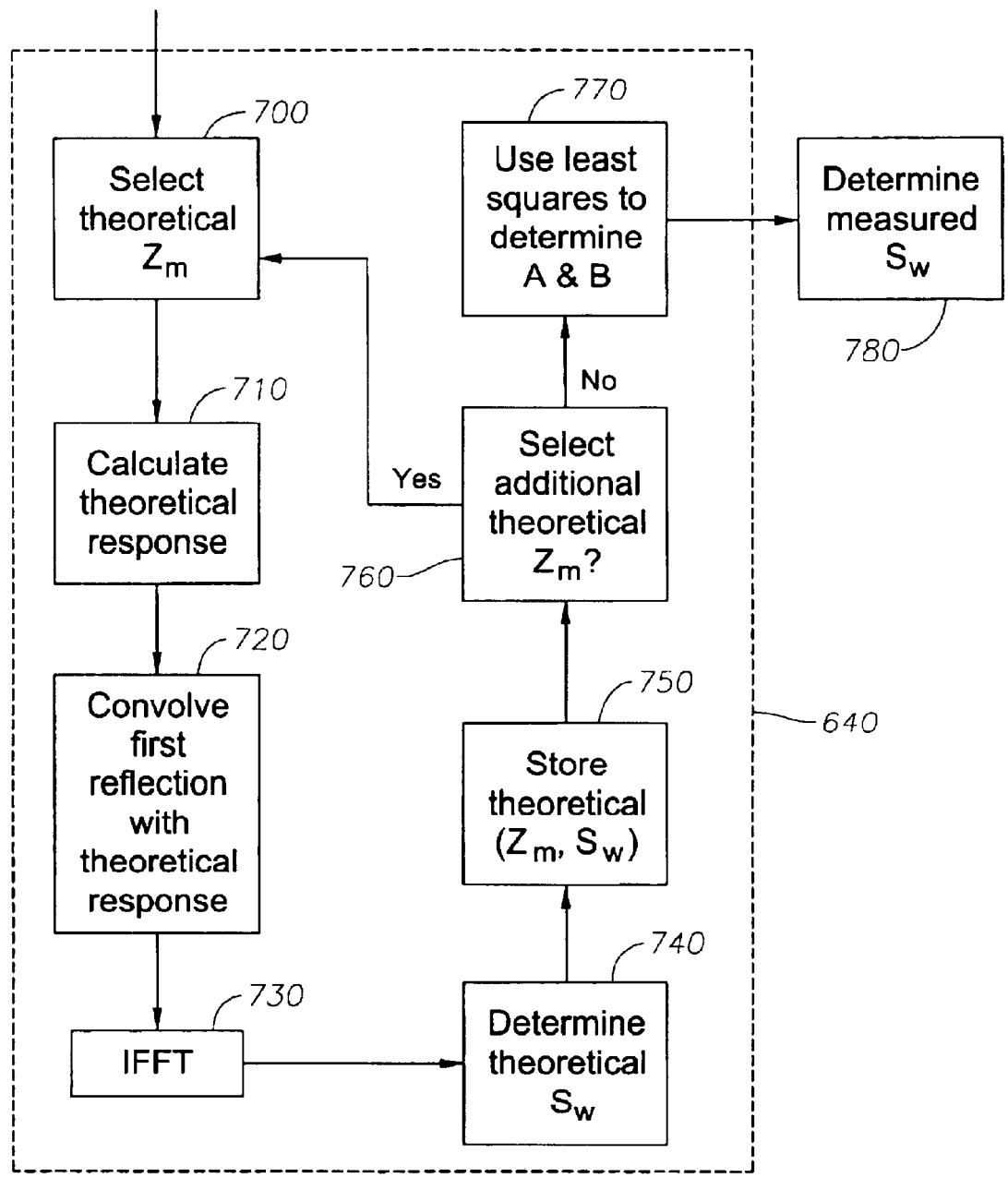
FIG. 7A is a flow diagram of a preferred embodiment.

FIG. 7A illustrates the curve fitting method, where a measurement equation is determined. As an initial matter, for a reverberation window of interest, $T_{win}$ the natural log of the sum of the reverberation waveform amplitude ($S_w$) varies linearly with well fluid impedance. That is, a linear relationship between well fluid impedance and $S_w$ may be expressed as:

$$Z_m = A + B \ln(S_w) \quad (3)$$

where $S_w$ is the sum of the reverberation waveform amplitudes and has the form:

$$S_w = \sum_t |x(t)| \quad (4)$$

the lower case x(t) being the amplitude at any given point in the reverberation waveform contained in $T_{win}$.

For the curve-fitting method, block 640 includes blocks 700–760. In block 700, an initial theoretical fluid impedance $Z_m$ is chosen. In block 710, the theoretical response R(ω) is calculated in accordance with Equation 2. In block 720, the first reflection is convolved with the theoretical response obtained in block 710. In block 730, the Inverse Fast Fourier Transform (IFFT) is performed to obtain a theoretical reverberation waveform. Next, the summed amplitudes of the theoretical reverberation waveform $S_w$ is determined in block 740. In block 750, the theoretical response R(ω) and reverberation waveform amplitude sum $S_w$ are stored. In block 760, it is decided whether or not additional data is needed. If additional data is necessary, another theoretical fluid impedance $Z_m$ may be chosen in block 700. To determine the coefficients in this linear relationship, steps 700–760 are repeated at least twice for different assumed fluid impedances $Z_m$. Each time, the resulting sum $S_w$ is calculated. From these multiple points, ($S_w$, $Z_m$), the coefficients A, B, can be determined using the least squares curve fitting in block 770. With the relationship, the measured impedance $Z_m$ can be determined from the observed $S_w$ using Equation 4 in block 780.

Lastly, in block 650 (FIG. 6), $S_w$ is substituted into Equation 3, and well fluid impedance $Z_m$, is determined. The acoustic velocity of the fluid may also be calculated in block 650. Because the separation between the transducer and disk is known, the velocity is calculable from the measured transit time $T_{tran}$. From the impedance (ρ) and velocity (v), the fluid density ($Z_m$) can be calculated due to the relationship: $Z_m = \rho v$.

As mentioned above, in a second embodiment, non-linear waveform inversion may be used in block 640 to determine the relationship between theoretical and measured reverberation. While the waveform inversion method is slower than the curve fitting method described above, it produces more accurate results because it matches entire reverberation waveform window using both amplitude and phase. As a result, many fluid acoustic properties including density and attenuation can be calculated simultaneously. A preferred method employs the Levenberg-Marquardt method. See generally W. Press et al., *Levenberg-Marquardt Method*, p. 542 (Numerical Recipes in C, 1988), incorporated herein by reference.

Figure 7B:
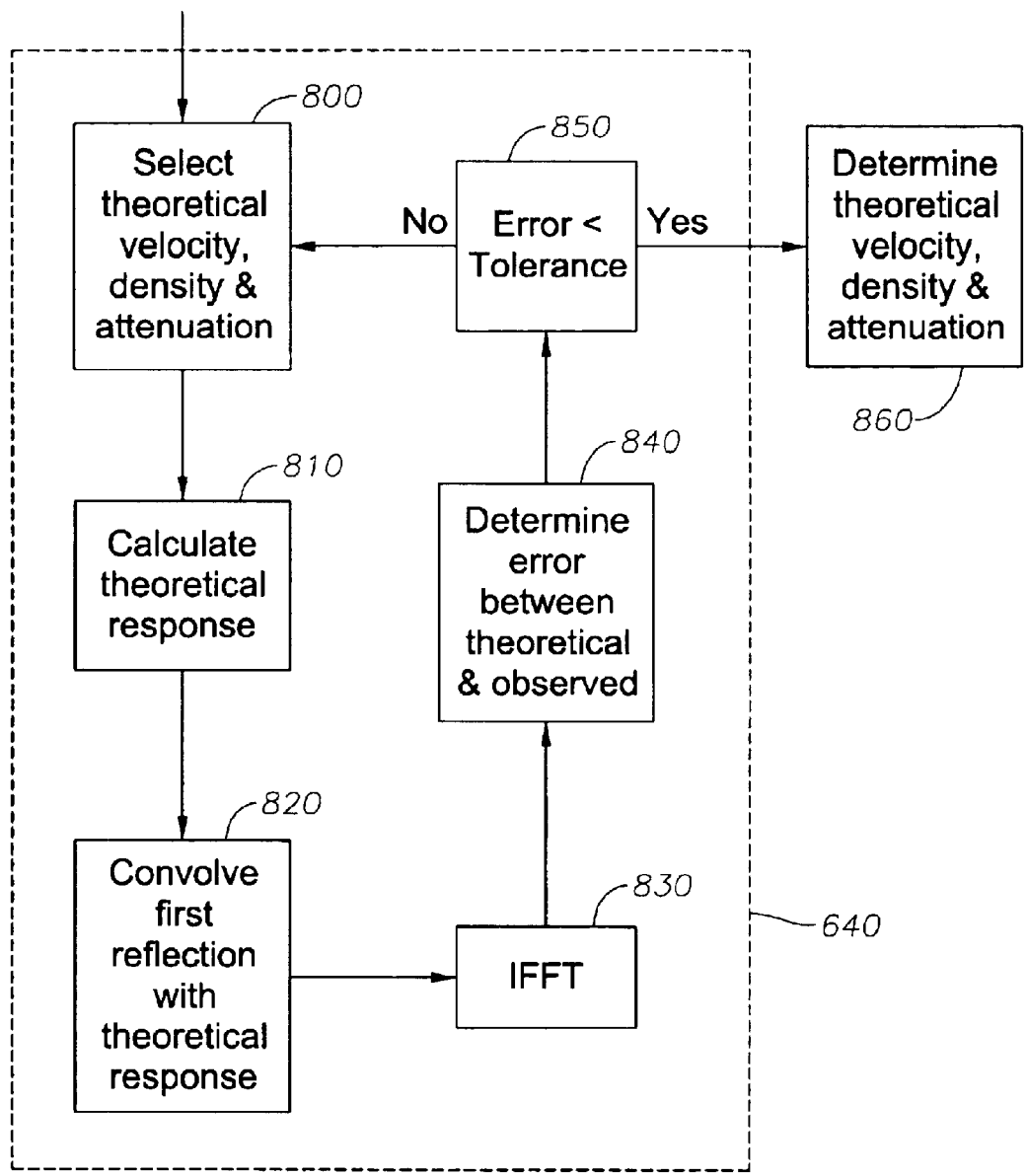
FIG. 7B is a flow diagram of a preferred embodiment.

In the non-linear waveform inversion embodiment shown in FIG. 7B, fluid properties such as velocity, density, and attenuation are initially estimated in block 800. In block 810, the theoretical response R(ω) is calculated in accordance with Equation 2. In block 820, the first reflection is convolved with the theoretical response obtained in block 710. In block 830, the Inverse Fast Fourier Transform (IFFT) is performed to obtain an estimated reverberation waveform. In block 840, the error between the estimated and measured waveforms is determined. The error is calculated according to Equation 5.

$$\text{Error} = \Sigma |(\text{observed} - \text{theoretical})^2| \quad (5)$$

In block 850, the error calculated in block 840 is compared to a predetermined tolerance. If the calculated error is greater that the predetermined tolerance, another estimate is performed in block 800 using the Levenberg-Marquardt method. This cycle is repeated until the calculated error is less than the predetermined tolerance. When the calculated error is less than the predetermined tolerance, the estimated fluid velocity, density, and attenuation are accepted as the measured properties in block 860.

While preferred embodiments of this invention have been shown and described, modifications thereof can be made by one skilled in the art without departing from the spirit or teaching of this invention. The embodiments described herein are exemplary only and are not limiting. For example, while the present invention has been described for use while drilling a well, it may also be used during completing and producing. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A tool for measuring one or more fluid properties that comprises:

a body having an associated volume through which a fluid may pass;

a known surface fixed within the volume to contact the fluid;

an acoustic transducer affixed to the body and configured to receive acoustic signal reflections and reverberations from the known surface; and a processor coupled to the acoustic transducer, wherein the processor calculates theoretical acoustic signal reverberations by combining a frequency domain response of the acoustic signal reflection with a theoretical frequency domain response of the known surface, and wherein the processor relates the received acoustic signal reverberations with the theoretical acoustic signal reverberations to determine the one or more fluid properties.

2. The tool of claim 1, wherein the known surface is metallic.

3. The tool of claim 1, wherein the known surface is steel.

4. The tool of claim 1, wherein the known surface is a metal disk.

5. The tool of claim 1, wherein the one or more fluid properties includes acoustic impedance.

6. The tool of claim 1, wherein the acoustic transducer is further configured to generate acoustic signals that impinge on the known surface to cause said acoustic signal reflections and reverberations.

7. The tool of claim 6, wherein the processor measures a time delay between the generation of the acoustic signals and the receiving of the acoustic signals to determine an acoustic velocity.

8. The tool of claim 1, wherein the one or more fluid properties includes fluid density.

9. A tool for measuring one or more fluid properties that comprises:
- a body having an associated volume through which a fluid may pass;
- a surface fixed within the volume to contact the fluid; and
- an acoustic transducer affixed to the body and configured to receive acoustic signal reflections and reverberations from the surface,
- wherein the surface has opposite sides configured to contact the fluid, and wherein the surface is a metal disk.

10. The tool of claim 9, further comprising a processor coupled to the acoustic transducer, wherein the processor calculates theoretical acoustic signal reverberations by combining a frequency domain response of the acoustic signal reflection with a theoretical frequency domain response of the metal disk, and wherein the processor relates the received acoustic signal reverberations with the theoretical acoustic signal reverberations to determine the one or more fluid properties.

11. The tool of claim 9, wherein the tool couples to a processor that measures a time delay between the generation of the acoustic signals and the receiving of the acoustic signals to determine an acoustic velocity.

12. The tool of claim 9, wherein the one or more fluid properties includes acoustic impedance.

13. The tool of claim 9, wherein the acoustic transducer is further configured to generate acoustic signals that impinge on the metal disk to cause said acoustic signal reflections and reverberations.

14. The tool of claim 9, wherein the one or more fluid properties includes fluid density.

15. A tool for measuring one or more fluid properties that comprises:
- a body having an associated volume through which a fluid may pass;
- a metal plate with opposite sides configured to contact the fluid, the plate being fixed within the volume to contact the fluid; and
- an acoustic transducer affixed to the body and configured to receive acoustic signal reflections and reverberations from the metal plate.

16. The tool of claim 15, further comprising a processor coupled to the acoustic transducer, wherein the processor calculates theoretical acoustic signal reverberations by combining a frequency domain response of the acoustic signal reflection with a theoretical frequency domain response of the metal plate, and wherein the processor relates the received acoustic signal reverberations with the theoretical acoustic signal reverberations to determine the one or more fluid properties.

17. The tool of claim 15, wherein the tool couples to a processor that measures a time delay between the generation of the acoustic signals and the receiving of the acoustic signals to determine an acoustic velocity.

18. The tool of claim 15, wherein the one or more fluid properties includes acoustic impedance.

19. The tool of claim 15, wherein the acoustic transducer is further configured to generate acoustic signals that impinge on the metal plate to cause said acoustic signal reflections and reverberations.

20. The tool of claim 15, wherein the one or more fluid properties includes fluid density.

* * * * *